(12) United States Patent
Bhadra et al.

(10) Patent No.: US 6,746,694 B1
(45) Date of Patent: Jun. 8, 2004

(54) HERBAL COMPOSITION FOR TREATING ASTHMA

(75) Inventors: Ranjan Bhadra, Calcutta (IN); Bikash Chandra Pal, Calcutta (IN); Krishna Das, Calcutta (IN); Samir Bhattacharaya, Calcutta (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/676,502

(22) Filed: Oct. 2, 2000

(51) Int. Cl.$^7$ .......................... A61K 35/78; A01N 65/00
(52) U.S. Cl. .................. 424/725; 424/769; 424/744; 424/774; 424/775; 424/776; 424/777; 424/778; 424/779
(58) Field of Search ................ 424/725, 744, 424/769, 774, 775, 776, 777, 778, 779

(56) References Cited

U.S. PATENT DOCUMENTS 6,541,045 B1 * 4/2003 Charters et al. ............ 424/737

FOREIGN PATENT DOCUMENTS

JP        7-138180    * 5/1995

OTHER PUBLICATIONS

Ramsewak et al "Biological Active Carbazole Alkaloids from Murraya keonigii" J. Agric. Food Chem vol. 47 pp. 444–447 (1999).*
Web site google.com:Ahmad Kartini Abstract "Chemical constituents of Murraya Koenigii (Rutaceae) and their biological activities" May 1999 Univ. Putra Malaysia Thesis—Goggle Web Site: Publication Type:Dissertation, Thesis Name of Candidate: Kartini uru.upm.edu.my/Research.nsf/ff29090c9567ef71c82565f700081f04/193ddd0ef0d81283482569a2000fedf2.*
Computer Dertwen ABS JP07138140 May 30, 1995.*
Computer CABI Abstract 1999:38735 Ramsewak et al "Jour Agric & Food Chem" (1999 vol. 47 No. 2 p 444–447.*

* cited by examiner

Primary Examiner—Herbert J. Lilling
(74) Attorney, Agent, or Firm—Birch, Stewart, Kolasch & Birch, LLP

(57) ABSTRACT

The invention relates to a novel composition containing an extract obtained from the plant *Murraya koenigii* and useful for the treatment or providing relief from acute asthma, and a process for the preparation of a lyophilized extract containing active principles of the plant *Murraya koenigii,* and a method for the treatment of asthma.

23 Claims, No Drawings

HERBAL COMPOSITION FOR TREATING ASTHMA

FIELD OF THE INVENTION

The present invention relates to the identification of a novel use of the principles extracted from the plant *Murraya koenigii* for treatment of asthma. This invention provides a process for the extraction of the principles from the plant *Murraya koenigii*. The invention also provides novel compositions useful in the treatment of asthma and methods for the treatment of asthmatic conditions using the said composition.

BACKGROUND AND PRIOR ART REFERENCES

Respiratory diseases such as asthma are reaching epidemic proportions in both the developed and developing world (Nature, Vol. 402, Supplement, and No. 6760, 1999. A special supplement on allergy and asthma). In countries such as Britain and Australia, the respiratory problem translates to 1 in 4 children under age of 14 years having asthma. The disease causes distress and misery in millions often at a time in their lives when they should be most active. Asthma interferes with sleep, intellectual functioning and recreational activities. At one extreme, asthma can be life threatening leading to occurrence to deaths that are avoidable.

Expert panel report has offered guidelines for diagnosis and management of asthma (JAMA Asthma Information Center, www.amaasssm.org/special/asthma/treatmnt/guide/guideline/gudelin.htm). Control of factors contributing to asthma severity is another avenue for management (JAMA Asthma Information Center, www.amaasssm.org/special/asthma/treatmnt/guide/guidelin/comp2/comp2.htm). several therapies and medications have also been suggested (JAMA Asthma Information Center, www.amaasssm.org/special/asthma/treatmnt/guide/guidelin/comp3/medicat/meditoc.htm and www.amaass.org/special/asthma/treatmnt/guide/guidelin/comp3/comp3.htm). Immunotherapy is another route for the treatment (JAMA Asthma Information Center, www.amasssm. or/special/asthma/treatmnt/guide/guidelin/comp2/immunoth.htm). Complementary alternative medicine is also being tried (JAMA Asthma Information Center, www.amaasssm.org/special/asthma/treatmnt/guide/guidelin/comp3/medicat/alternat.hmt) However, no satisfactory medication for cure of the disease has been found.

Herein the active factors in *Murraya koenigii* was prepared and used under in vitro system to show its usefulness for relief, treatment and cure of asthmatic problem. The plant *Murraya koenigii* has been studied and reported to have various medicinal values (Chakraborty, M. P Phytochemistry 1997, October; Khan B. A, Indian J of Expt. Biol. 1997 February; Khan B A Indian J of Physiology and Pharmacology 1996, April; Khan B A Plant Foods Hum. Nutr. 1996 June).

The leaf of this plant is widely used in various food preparations in India. Further, the plant is ubiquitous. Thus the prior art suggests that the extracts of the plant have several medicinal and other properties which have been widely investigated. This is adequate proof that the extracts of the plant can be safely consumed by humans without any side effects.

The inventors undertook a study on the extracts of this plant to identify the therapeutic principles of the plant. During their study, the inventories discovered the presence of the active principles in the leaf of *Murraya koenigii* which surprisingly were found to be useful in the treatment and cure of asthma.

OBJECTIVES OF THE INVENTION

The main objective of the present invention is to provide a method for the treatment of asthmatic conditions employing active principles extracted from the plant *Murraya koenigii*.

Another object is to provide a process for the isolation of active principles from the plant *Murraya koenigii* and use the same for relief, treatment and cure of asthma.

Yet another object is to provide a simple, fast and inexpensive process to obtain a mixture of active (four) compounds possessing biological activities useful in the treatment of asthma.

Still another object is to provide novel compositions containing active principles extracted from the plant *Murraya koenigii* and useful in the treatment of asthma.

SUMMARY OF THE INVENTION

Accordingly, the present invention provides a method for the treatment of asthma, employing principles extracted from the plant *Murraya koenigii*. The invention also provides novel compositions useful in the treatment of asthma and methods for the extraction of active principles from the plant *Murraya koenigii*.

DETAILED DESCRIPTION OF THE INVENTION

Accordingly, the invention provides a process for preparing an extract from the plant *Murraya koenigii*, useful in the treatment of asthma, said process comprising the steps of pulverising plant materials obtained from plant *Murraya koenigii*, extracting the plant material with a solvent at ambient temperature, concentrating the extract by filtering and evaporating it under reduced pressure and lyophilizing the concentrate to obtain a lyophilized extract containing active principles of the plant *Murraya koenigii*.

In an embodiment, the plant materials are obtained from plant parts of *Murraya koenigii* selected from garden fresh leaves or leaves dried under shade.

In another embodiment, the leaves are pulverized by conventional methods to get homogenized leaves.

In yet another embodiment, the plant materials are extracted with solvents selected from hydrocarbon solvents, chlorinated solvents, ester solvents, ketonic solvents, alcohols, water and buffers.

In still another embodiment, the solvents are selected from the group consisting of petroleum ether (BP 40–60° C.), petroleum ether (60° C.–80° C.), benzene, pentane, hexane, chloroform, dichloromethane, carbon tetrachloride, diethyl ether, tetrahydrofuran, dioxane, acetone, cyclopentanone, ethyl acetate, ethyl formate, methanol, ethanol, n-butanol, water and buffers. In another embodiment, the concentration of the extract is effected by filtering and evaporating the solvents under reduced pressure at a temperature range of 20° C.–80° C. preferably at ambient temperature and lyophilizing the concentrate by conventional methods to obtain mixtures of the active factors.

In yet another embodiment, the extract obtained from the plant *Murraya koenigii* comprises active principles which dark colored solids soluble in dimethylsulfoxide.

In another embodiment, the active principles obtained from the plant *Murraya koenigii* are biocompatible and non-toxic in nature. The active principles have $R_f$ values 0.73, 0.60, 034 and 0.14 in chloroform and methanol in the ratio 19:1 and $R_f$ values 0.60, 0.38, 024 and 0.15 in the chloroform. The active principles have four peak with retention time 3.37, 3.49, 4.0 and 5.69 in methanol as solvent at 254 nm. The extraction process is carried out for a period ranging from 1–120 hrs, preferably between 12–16 hrs.

Further, the invention also provides pharmaceutical composition useful in the treatment of asthma, said composition comprising an effective amount of extract obtained from the plant *Murraya koenigii* together with, or optionally associated with a pharmaceutically acceptable additive. The additives used in the composition comprise powder or extracts of plants selected from *M. panicitlate Linn, H. abelmoschus, T ammi, S. aromaticum, A. vasica Nees, E hirta,* and *M. koinegii*. These additives are present in the range of 80–100 mg of *M. paniculate Linn*, 40–60 mg of *H. abelmoschus*, 38–62 mg of *T. ammi*, 7–13 mg of *S. aromaticum*, 85–115 mg of *A. vasica Nees* and 90–110 mg of *E hirta*.

In an embodiment, the composition comprises

| | |
|---|---|
| *M. paniculata* Linn. Syn. *M exotica* (KAMINI) | 90 mg |
| *H. abelmoschus* (JOWAN) | 50 mg |
| *T. ammi* (LAVANGA) | 50 mg |
| *S. aromaticum* (BASAK) | 10 mg |
| *A. vasica* Nees (PUSITOA) | 100 mg |
| *E. hirta* | 100 mg |
| *M. koinegii* (Suravi Neem) | 100 mg |

In the said composition, the extract of the plant M. koiitegii is present in the range of 87–105 mg per dose. In the said composition, the extract of the plant *M. koinegii* comprises active principles which are dark colored solids, soluble in dimethylsulfoxide. The active principles have $R_f$ values 0.73, 0.60, 034 and 0.14 in chloroform and methanol in the ratio 19:1 and $R_f$ values 0.60, 0.38, 024 and 0. 15 in the chloroform. These principles have four peaks with retention time 3.37, 3.49, 4.0 and 5.69 in methanol as solvent at 254 nm. The said active principles obtained from the plant *M. koinegii* exhibit antioxidant property i.e. $O_2$ inhibition.

Further, the invention provides a method for the treatment of asthma, said method comprising the steps of administering an effective amount of the composition comprising an extract obtained from the plant *Murraya koenigii* and at least one pharmaceutically acceptable additive to a subject in need thereof.

In an embodiment, the lyophilized extract obtained from *Murraya Koenigii* is administered alone or along with other conventional additives for the treatment of asthma. In still another embodiment, the mode of administration is oral for the treatment of mild or acute asthma.

In yet another embodiment, the dosage level of the composition, comprising the extract from the plant *Murraya koenigii* is between 325–600 mg twice daily for the period ranging from 3 to 30 days.

In another embodiment, the dosage level is in between 325–600 mg twice daily for the period ranging from 3 to 15 days for mild asthmatic condition, and 15–30 days for acute asthmatic condition.

In still another embodiment, the additives are selected from *M. panicutlate Linn, H. abelmoschus, T. ammi, S. aromaticum, A. vasica Nees, E hirta,* and *M. koinegii*.

As said above, the additives are present in a range of 80–100 mg of *M. paniculate Linn*, 40–60 mg of *H. abelmoschus*, 38–62 mg of *T. ammi*, 7–13 mg of *S. aromaticum*, 85–115 mg of A. vasica Nees, 90–110 mg off *E. hirta*, and 87–105 mg of M. *koinegii*. per dose.

In another embodiment, the additives obatined from *M. paticulate Linn, H. abelmoschus, T. ammi, S. aromaticum A. vasica Nees, E. hirta,* and *M. koinegii* are administered to include properties such as antidiahorial, antiseptic, carminative, stimulation, anti-cough, anti-bronchitis and nourishment.

In another embodiment, the additives obtained from *M. paniculate Linn, H. abelmoschus, T. ammi, S. aromaticum, A. vasica Nees, E hirta,* and *M. koinegii* are administered to include properties such as antidiarrheal, antiseptic, carminative, stimulation, anti-cough, anti-bronchitis and nourishment.

In addition, the invention provides an anti-oxidant composition for human beings and animals, said composition comprising a effective amount of extract obtained from the plant *Murraya koenigii* together with or optionally, associated with pharmaceutically acceptable additives.

In still another embodiment, the additives comprise powder or extracts of plants selected from *M. pamiclate Linn, H. abelmoschus, T. ammi, S. aromaticum, A. vasica Nees, E hirta,* and *M. koinegii*.

In an embodiment, the additives are present in a range of 80–100 mg of *M. paniculate Linn*, 40–60 mg of *H. abelmoschus*, 38–62 mg of *T. ammi*, 7–13 mg of *S. aromaticum*, 85–115 mg of *A. vasica Nees*, 90–110 mg of *E hirta*, and 87–105 mg of *M. koinegii*. per dose of the anti-oxidant composition.

As said above, the active factor(s) in *Murraya koenigii* useful for relief, treatment and cure of asthmatic problem(s), the preparation of which comprises drying, powdering, and extracting the dried leaves of the plant, *Murraya koenigii*, in a percolator at an ambient temperature using appropriate solvents and concentrating the extract under reduced pressure and finally lyophilizing the concentrate to make the active factor(s).

In the present invention, active factor(s) in *Murraya koenigii* for the treatment and cure of asthmatic problem are prepared from the leaves of the plant by drying, powdering and extracting, in a percolator at an ambient temperature using appropriate solvents and concentrating the extract under reduced pressure and finally lyophilizing the concentrate to make the active factors.

In an embodiment of the present invention, the active factors from the plant material to be used as an oral preparation for relief, treatment and cure of asthmatic problem.

In another embodiment of the present invention, the leaf of *Murraya koenigii* used was garden fresh or fresh leaf dried under sun or shade.

In still another embodiment of the present invention, plant material was used for the extraction with appropriate solvents such as methanol or water or buffers in a percolator.

In yet another embodiment of the present invention, the plant extract made by the methanol/appropriate solvent or water was concentrated under reduced pressure to get the mixture of active factor.

In yet another embodiment of the present invention, the concentrate of the plant extract was lyophilized to make the factors free of solvent or water.

In yet another embodiment of the present invention, lyophilized solid obtained as the mixture of active factors present in the leaf of *Murraya koenigii* was proposed to be used for relief, treatment and cure of asthmatic problem.

The method of preparation of the active factors comprises the following
  1) collecting the fresh leaves from the local suppliers,
  2) drying the leaves under shade to a moderate degree or to take the fresh leave as the starting material,
  3) powdering the dried or homogenizing the fresh leaves in the apparatus known in the art, 4) putting the powder or homogenate in a percolator under the bulk of appropriate solvents; choosing hydrocarbon solves such as petroleum ether (B.P 40–60° C.), petroleum ether (B.P 60–80° C.), pentane, hexane, benzene etc.; chlorinated solvents like chloroform, dichloromethane, carbon tetrachloride etc.; etherial solvents such as diethyl ether, tetrahydrofuran, dioxane etc., ketonic solvents such as acetone, cyclopentanone etc.; ester solvents such as ethyl acetate, ethyl formate etc; all alcohol such as methanol, ethanol, n-butanol etc.; water and buffers, 5) extracting the percolated plant material using a percolator or the apparatus or equipment currently known in the art over a period of time ranging from 1 to 120 hours, 6) evaporating the solvent under reduced pressure using an apparatus or equipment currently known in the art at a temperature ranging from 20 to 80° C., 7) lyophilizing or drying the material in the apparatus or equipment currently known in the art, 8) storing the processed material in a cool and dry place in an air tight container, and 9) evaluating the bioactivity of the material.

The following examples are given by way of illustration and therefore should not be construed to limit the scope of the present invention.

Collection of Plant Material

The leaves of *M. koenigii* were collected from shrubs in the month of March–August 2000 from different areas of West Bengal, India. A voucher specimen is deposited at the department of Medicinal Chemistry at the Indian Institute of Chemical Biology, 4, Raja S. C. Mallick Road, Calcutta-700 032.

Preparation of the Active Factors or Material

EXAMPLE—1

Fresh leave containing branches of *Murraya koenigii* collected, cleaned and washed with water after getting from the local supplier and used as starting material. It was air-dried under shade and drying continued till it was brittle to make suitable for powdering in grinder-mixture.

87 gm. of the powdered leaves *Murraya koenigii* was placed in a glass percolator (5-litr. capacity) with the addition of 1000 ml. of methanol so as to submerge the material satisfactorily. This was kept for 12 to 16 hrs (over night) at room temperature. Filtering the extract through Whatman No. 1 filter paper collected the percolate. The process of extraction was repeated four times and the combined extract was evaporated to dryness under reduced pressure in a rotary evaporator keeping the temperature at 40° C. (bath). The solid residual matter left was viscous in appearance and it was further dried by lyophilization. The yield was 14.84 gm. and the material was tested and found biologically active in both neutrophil or ex vivo blood system.

EXAMPLE—2

The leaves of *Murraya koenigii* air dried and weighing 90 gms., was powdered and taken in a percolator. It was dipped in 800-ml chloroform. The submerged material was allowed to be extracted by the solvent for 12 to 16 hours (over night). The extract was filtered through Whatman No. 1 filter paper and collected; this process was repeated for three times. The extract was evaporated to dryness in flash evaporator under reduced pressure at 40° C. The residual substance was then dried in a desiccator under high vacuum and the solid mass weighing 11.5 gm was tested and found biologically active.

EXAMPLE—3

150 gm of fresh leaves of *Murraya koenigii* thoroughly washed in sterile water was homogenized with 750 ml of glass distilled water in a mixture-blender and then sonicated in an ultra sonic bath with 15 burst, each for 5 min. Filtering through Whatman no. 1 filter paper separated the material extracted in water. This type of treatment for extraction was repeated for three times. The combined extract was lyophilized yielding a powdered material, 11 gm in weight. This was then tested for biological activity.

Properties of the Materials

The biologically active material obtained by examples 1 or 2 or 3 has the following properties:

1. The dried solid prepared as stated above was a dark coloured material soluble in DMSO or dimethyl sulfoxide.

2. Thin layer chromatography of the active material shows four spots having Rf.0.60, 0.38, 0.24, and 0.15 in the solvent system of chloroform and Rf 0.73,0.60,0.34 and 0.14 in solvent system chloroform and methanol (19:1).

3. The HPLC analysis of the active material using Intersil ODS-3 (4.6×250 mm) analytical column, solvent system methanol and a flow rate 1.0 ml/min., detection at 254 nm resolved the material into four peaks with the retention time 3.37, 3.49, 4.00, and 5.69 mins.

Evaluation of the Activity in an in vitro System

Biological evaluation was carried out as per the following procedure.

a) Inhibition of Arachidonic Acid Oxidation in Presence of the Active Material by Neutrophil Human peripheral blood neutrophil was prepared by standard method [Downey, G. P., Fukushima, T., Fialkow, L. and Waddel, T. K. (1995) Semin. Cell Biol. 6 345]. In brief, heparinised blood treated with 2% gelatin (in normal saline) for half an hour to allow the RBC separation at the bottom. The rest of the mixture was taken and subjected to gradient separation using Histopaque and carrying out the centrifugation (at 1400 rpm at room temp. for 12 min.). The neutrophil available as a separate layer at the bottom was collected and then made into suspension in sterile PBS or phosphate buffered saline.

(i) The neutrophil (1×104/well of 24 well tissu culture plate) was treated with active material (20 (g/ml) for 60 min., while control did not contain any active material.

(ii) The neutrophil primed with Phorbol Myristic Acetate (PMA) (10(M) for 30 min. Followed by addition of active material (20 (g/ml) or without it for 30 mins.

(iii) The neutrophil treated with active material (20 (g/ml) for 30 min. followed by PMA (10(M) activation for 30 min.

The oxygen consumption by the treated neutrophil was measured after ten minutes of the addition of arachidonic acid 10(1 (12.2 mg/ml in absolute alcohol) (Method. Enzymol. Ed. By Murphy, R. C, and Fitzpatrick F. A. vol 187 pp-268), in 2 ml volume of neutrophil suspension. The assay of the oxygen consumption was carried out by oxygen sensor (of Hansatec with O2 electrode control having Clark type probe). The results of inhibition of oxygen consumption due to arachidonic acid oxidation are given in Table-1

TABLE 1

Inhibition of arachidonic acid oxidation by neutrophil

| Treatment | Micromole oxygen consumed/10 min | % of inhibition of $O_2$ consumption by active material with respect to Stimulation | Without stimulation |
|---|---|---|---|
| A. Phosphate Buffered Saline 60 min. | 16.08 | NA | — |
| B. Active extract 60 min in Phosphate Buffered Saline | 12.85 | — | 20 |
| C. Phorbol Myristic Acetate for 30 min. | 39.58 | — | — |
| D. Calcium ionophore for 30 min. | 64.01 | — | — |
| E. Active extract 30 min + PMA 30 min. | 21.42 | 46 | — |
| F. Active extract 30 min. + Calcium ionophore 30 min. | 25.3 | 60 | — |

Calcium ionophore gave better results as there was about 60% inhibition while PMA effects 46% inhibition of $O_2$ consumption by active material present in *Murraya koenigii* leaf under in vitro neutrophil test. In both the stimulation remarkable inhibition of $O_2$ consumption indicates the efficacy of the material.

The results in Table-1 illustrated that the active factors in *Murraya koenigii* leaf acted as an inhibitor of oxygen consumption in presence of normal as well as activated human neutrophil and arachidonic acid. It suggested that oxidation of arachidonic acid is strongly inhibited by active factors present in *Murraya koenigii* leaves. The leukotrienes are the biological mediators of asthtna and the oxidation of arachidonic acid is the rate-determining step for the synthesis of the leukotrienes. The strategy of asthma drug development is to search or synthesize compounds or prepare substances that inhibit the synthesis of leukotrienes or precisely cause the inhibition of the oxidation of arachidonic acid. The active material or compounds prepared here not only inhibit the oxidation of arachidonic acid but also expected to be free of toxicity and compatible for use in human as the plant leaves are extensively used as food ingredients. Hence it qualifies as a drug for asthma.

b) Inhibition of Arachidonic acid Oxidation in Presence of the Active Material by Human ex vivo Blood.

500 μl of heparinised human whole blood was taken in each well of a 6-well micrometer plate to which the *Murraya koenigii* active material or none was added to have a final concentration of 50(g/ml when the total volume was adjusted to 2 ml. with PBS. The plates were incubated for 2 hours with constant shaking. Next 10 μl of arachidonic acid (12.2 gm/ml in absolute alcohol stored under argon at –200 C.; Method. Enzymol. Ed. By Murphy, R. C, and Fitzpatrick F. A. vol. 187 pp-268) was added to each well for 10 mins. Prior to the addition of Phorbol Myristic Acetate (PMA, 10(M) or calcium ionophore A23187 (20(g/ml), (Spaethe S. M, Snyder D. W, Pechous P. A, Clarke T, VanAlstyne E. L Biochem. Pharmacy. 43; 1992,377–82). After 30 mins of the addition of the stimulator, a YSI Clark oxygen probe containing oxygen-monitoring equipment monitored oxygen consumption.

TABLE 2

Inhibition of arachidonic acid in whole human ex vivo blood in presence of *Murraya koenigii* leaf material

| Addition | Oxygen consumption (in nmol)/ 10 mins | Inhibition % of control |
|---|---|---|
| A. None N1(PMA treated) | 39.99 | — |
| B. None N2 (Ca + ionophore) | 62.41 | — |
| C. None N3 (patient's blood) | 32.15 | — |
| D. Whole leaf in N1 blood | 22.1 | 45 |
| E. Water extract in N1 blood | 18.56 | 54 |
| F. Methanol extract in N1 blood | 10.70 | 73 |
| G. Methanol extract in N2 blood | 18.21 | 73 |
| H. Methanol extract in N3 blood | 11.70 | 70 |
| Chloroform extract in N1 blood | 11.11 | 72 |

*Patient having Eosinophil count 13 with 7 years of chronic asthma.

The Nitro Blue Tetrazolium reduction test was also found highly effective in presence of the leaf preparation demanding it to be a powerful antioxidant.

Again, the Nitro Blue Tetrazolium (NBT) reduction test was carried out as per the standard procedure [Rouiller, Y. B., and Mauel J.(1987) Infec.Immun. 55, 587]. Neutrophil was prepared and treated with or without PMA (30 min.) and followed by leaf extract (60 min.) or without it. Then 100(1 of NBT solution (3 mg/ml) was added and cells were incubated for various intervals (0 to 120 mins). Formazan deposition was measured at 550 nm in an ELISA reader (Labsystem Multi Skan MS). The results showed that the activation of neutrophil with PMA was strongly inhibited about 6 times in the presence of the active material from the Murray koenigii leaves at 120 min. The leaf preparation has strong antioxidant property which lend a firm support to recuperate from the condition occurs during asthma.

More over we shall see that the freshness is a must as because one of volunteer patients takes cooked the leaves in his food but his severe attack was not influenced with such a material.

| LOCAL NAMES | PARTS SELECTED | AMOUNTS |
|---|---|---|
| KAMINI (*M. paniculata* Linn. Syn. *M exotica*) | Bark of root | 80–100 |
| LATAKASTURI (*H. abelmoschus*) | Seed | 40–60 |
| JOWAN (*T. ammi*) | Fruit | 38–62 |
| LAVANGA (*S. aromaticum*) | Dried flower buds | 7–13 |
| BASAK (*A. vasica* Nees) | Leaves | 85–115 |
| PUSITOA (*E hirta*) | Whole plant | 90–110 |
| Suravi Neem *M. koinegii* | Root bark and leaves | 87–105 |

The leaves of these plants are frequently used as flavor enhancer in South Indian cooked food. However, heating of the leaves denatures its anti-asthmatic property. Its use as a cooking item or in food recipe is known for more than centuries and no untoward occurrence is yet evident indicating all components of this leaf as totally safe for human consumption. Use of this plant especially in South Indian food never produced bowel discomfort or vomiting or stomach upset or any other problem. From all these information it is quite convincing that any preparation from this leaf as a drug for asthma will be absolutely safe.

The leaves of the plants are used as flavor enhancer in cooked food in most of the parts of India. The use is known for centuries and till date no untowards effects is reported from any corner. Especially it is neither bitter in taste nor odd in taste. After taking the leaf preparation no bowel discomfort or vomiting or stomach upset or any gastrointestinal problem was reported from any of the healthy volunteers. It was taken twice daily over a period of 30 days and found totally satisfactory without any complain from any of the healthy volunteers.

Five patients volunteer (both female and male) were chosen with respect to their asthmatic condition depending on their sensitivity to the different causative agents that manifest their asthma.

Case—I

A female patent known for dust and cold sensitive severe asthma suffering for last seven years. Chest tightness, whezee, cough, severe shortness of breathing, night sleeplessness and huge mucus secretion during late night hours were the primary symptoms. She had to take inhaler twice or thrice daily.

For medication two spoonful whole plant preparation were taken by her twice daily for fifteen days that observations were as follows:
  a) Currently she did not have to take inhaler except occasionally once in a day.
  b) Wheeze and cough had been totally stopped.
  c) She is now completely free from chest tightness.
  d) She appears physically normal and capable of taking strenuous walking like stepping up staircase to cross floors up to third level.

Case—II

Two volunteer patients (one male and another female) with a genetic predisposition for asthma had sleepiness during night time and were very prone to asthmatic episodes due to sensitivity to the city pollution. Shortness of breathing was their main complaint, and one had to take an inhaler when a severe night attack occurred. They followed the medication as described in Case-I above for one month.
  i) During nine months of observation, they did not have any asthmatic attacks,
  ii) No shortness of breath was reported by them,
  iii) In the case of the male patient, his smoking was a risk enhancer for an asthmatic attack. However, he did not have any breathing discomfort due to smoking even exceeding his regular schedule.
  iv) The female patient had shortness of breath when she took long walks or climbed even a single staircase, but during treatment, she did not have any trouble breathing even when she climbed up to the third level.

Case—III

Another young volunteer patient who has periodically severe attack with acute shortness of breathing and it was usual practice that he had to take in hospital for fresh oxygen supply to ease out breathing acuteness.

During one such episode of acute attack of shortness of breathing, he took the leaf preparation and the inference are:
  i) He did not have to attend hospital,
  ii) Since then he took this medication for a month, and
  iii) His every day activity has been increased remarkable till date there is no occurrence of highly acute respiratory distress.

Case—IV

An aged woman patient suffering from sleeplessness during night and extreme shortness of breathing and showing no response to the modern medication including inhaler.

She was medicated with the leave preparation taking twice daily for fifteen day and her condition has improved remarkably.

Thus, the application herein providing a sample, fast inexpensive process for preparation of a plant material from an abundantly available plant for relief, treatment and cure of asthmatic problem satisfactorily. The method of administration of the plant material is also simple. The success rate time is 100% among the volunteer. There has been no case of relapse during the observation time of 6 months. No adverse or side effect was found after the treatment.

The major advantages of the present invention are:
1. It is expected to provide relief, treatment and cure of asthmatic problem satisfactorily.
2. It is prepared from a plant material, which is used in food for centuries.
3. The plant material is biocompatible and non-toxic as it is consumed along with food.
4. The plant is abundantly available.
5. Method of preparation of the active material/principle is simple, fast and inexpensive.
6. Its cultivation and propagation will be easy and it grows in all kinds of soil.

What is claimed is:

1. A pharmaceutical composition useful in the treatment of asthma, said composition comprising an amount of an extract obtained from the plant *Murraya koenigii* effective for treating asthma together with at least one pharmaceutically acceptable additive;

wherein said extract is made by a process comprising:
  i) extracting fresh leaves of *Murraya koenigii* with a solvent to obtain a percolate, said solvent being selected from the group consisting of a hydrocarbon solvent, a chlorinated hydrocarbon solvent, an alcohol solvent, an ether solvent and an ester solvent,
  ii) separating the percolate from the leaves, and
  iii) removing the solvent from the percolate to obtain said extract; and wherein the at least one additive is a powder of a plant selected from the group consisting of *Murraya paniculate Linn, Hibiscus abelmoschus, Trachyspenmum ammi, Syzygium aromaticum, Adhatoda vasica Nees* and *Euphorbia hirta.*

2. The composition as claimed in claim 1, wherein the composition comprises 80–100 mg of *Murraya paniculate Linn,* 40–60 mg of *Hibiscus abelmoschus,* 38–62 mg of *Trachyspermum ammi,* 7–13 mg of *Syzygium aromaticum,* 85–115 mg of *Adhatoda vasica Nees* and 90–110 mg of *Euphorbia hirta.*

3. The composition as claimed in claim 1, comprising:

| | |
|---|---|
| *Murraya paniculata* Linn. Syn. *M. exotica* (KAMINI) | 90 mg |
| *Hibiscus abelmoschus* (JOWAN) | 50 mg |
| *Trachyspermum ammi* (LAVANGA) | 50 mg |
| *Syzygium aromaticum* (BASAK) | 10 mg |
| *Adhatoda vasica* Nees | 100 mg |

-continued

| (PUSITOA) | |
|---|---|
| *Euphorbia hirta* | 100 mg |
| *Murraya koenigii* | 100 mg. |
| (Suravi Neem) | |

4. The composition as claimed in claim 1, wherein the extract of the plant *Murraya koenigii* is present in the range of 87–105 mg per dose.

5. The composition as claimed in claim 1, wherein the extract has active principles having $R_f$ values 0.73, 0.60, 0.34 and 0.14 in chloroform and methanol in the ratio 19:1 and $R_f$ values 0.60, 0.38, 0.24 and 0.15 in chloroform.

6. The composition as claimed in claim 1, wherein the extract exhibits four peaks having retention times of 3.37, 3.49, 4.0 and 5.69 minutes in high pressure liquid chromatography over octyl decyl silane medium using methanol solvent and detection of absorbance at 254 nm.

7. The composition as claimed in claim 1, wherein the extract obtained from the plant *Murraya koenigii* exhibits antioxidant activity.

8. A method for the treatment of asthma in a patient in need thereof, said method comprising:
  administering to the patient an amount of a composition comprising an extract obtained from the plant *Murraya koenigii* obtained by a process comprising:
   i) extracting fresh leaves of *Murraya koenigii* with a solvent to obtain a percolate, said solvent being selected from the group consisting of a hydrocarbon solvent, a chlorinated solvent, an ester solvent, an alcohol solvent, water and a buffer;
   ii) separating the percolate from the leaves; and
   iii) removing the solvent from the percolate to obtain said extract.

9. The method as claimed in claim 8, wherein the extract obtained from *Murraya koenigii* is lyophilized.

10. The method as claimed in claim 8, wherein the mode of administration is oral for the treatment of mild or acute asthma.

11. The method as claimed in claim 8, wherein the dosage level of the composition is in between 325–600 mg twice daily for the period ranging from 3 to 30 days.

12. The method as claimed in claim 8, wherein the dosage level is in between 325–600 mg twice daily for the period ranging from 3 to 15 days for mild asthmatic condition.

13. The method as claimed in claim 9, wherein a powdered additive is added to the lyophilized extract, the powder being of at least one selected from the group consisting of *Murraya paniculate Linn, Hibiscus abelmoschus, Trachyspermum ammi, Syzgium aromaticum, Adhatoda vasica Nees* and *Euphorbia hirta*.

14. The method as claimed in claim 13, wherein the composition comprises 80–100 mg of *Murraya paniculate Linn*, 40–60 mg of *Hibiscus abelmoschus*, 38–62 mg of *Trachyspermum ammi*, 7–13 mg of *Syzygium aromaticum*, 85–115 mg of *Adhatoda vasica Nees*, 90–110 mg of *Euphorbia hirta*, together with 87–105 mg of *Murraya koenigii* per dose.

15. The method as claimed in claim 14, wherein the composition comprises 90 mg of *Murraya paniculate Linn*, 50 mg of *Hibiscus abelmoschus*, 50 mg of *Trachyspermum ammi*, 10 mg of *Syzygium aromaticum*, 100 mg of *Adhatoda vasica Nees*, 100 mg of *Euphorbium hirta*, along with 100 mg of *Murray koenigii* per dose.

16. The method as claimed in claim 9, wherein the composition comprises the additives *Murraya paniculate Linn, Hibiscus abelmoschus, Trachyspermum ammi, Syzygium aromaticum, Adhatoda vasica Nees, Euphorbium hirta*, and is also effective as an antidiarrheal, antiseptic, carminative, stimulant, antitussive, anti-bronchitis agent and for nourishment.

17. The method as claimed in claim 13, wherein the additives are obtained from:
  bark or root of *Murraya paniculate Linn;* dried flower buds of *Hibiscus abelmoschus;* leaves of *Trachyspermum ammi;* whole plant parts of *Syzygium aromaticum;* root of *Adhatoda vasica Nees* and bark of *Euphorbium hirta*.

18. A pharmaceutical composition having an antioxidant activity, said composition comprising an antioxidant effective amount of an extract obtained from the plant *Murraya koenigii* together with at least one pharmaceutically acceptable additive;
  wherein said extract is made by a process comprising:
   i) extracting fresh leaves of *Murraya koenigii* with a solvent to obtain a percolate, said solvent is selected from the group consisting of a hydrocarbon solvent, a chlorinated hydrocarbon solvent and an ether solvent;
   ii) separating the percolate from the leaves; and
   iii) removing the solvent from the percolate to obtain said extract; and
  wherein the at least one additive is a powder of a plant selected from the group of *Murraya paniculate Linn, Hibiscus abelmoschus, Trachyspennum ammi, Syzygium aromaticum, Adhatoda vasica Nees* and *Euphorbium hirta*.

19. The composition as claimed in claim 18, wherein the composition comprises 80–100 mg of *Murraya paniculate Linn*, 40–60 mg of *Hibiscus abelmoschus*, 38–62 mg of *Trachyspermum ammi*, 7–13 mg of *Syzygium aromaticum*, 85–115 mg of *Adhatoda vasica Nees*, 90–110 mg of *Euphorbium hirta*, together with 87–105 mg of *Murraya koenigii* per dose.

20. The composition as claimed in claim 19, wherein the composition comprises 90 mg of *Murraya paniculate Linn*, 50 mg of *Hibiscus abelmoschus*, 50 mg of *Trachyspermum ammi*, 10 mg of *Syzygium aromaticum*, 100 mg of *Adhatoda vasica Nees*, 100 mg of *Euphorbium hirta*, together with 100 mg of *Murraya koenigii* per dose.

21. The composition as claimed in claim 18, wherein the additives *Murraya paniculate Linn, Hibiscus abelmoschus, Trachyspermum ammi, Syzygium aromaticum, Adhatoda vasica Nees, Euphcrbium hirta* along with *Murraya koenigii* are used as an antidiarrheal, antiseptic, carminative, stimulant, antitussive, anti-bronchitis agent and nourishment, respectively.

22. The composition as claimed in claim 18, wherein the additives are selected from *Murraya paniculate Linn, Hibiscus abelmoschus, Trachyspermum ammi, Syzygium aromaticum, Adhatoda vasica Nees* and *Euphorbium hirta*, in the form of bark or root; seed; fruit; dried flower buds; leaves; whole plant; and root and bark, respectively.

23. The method as claimed in claim 21, wherein the dosage level is in between 325–600 mg twice daily for the period ranging from 15–30 days for acute asthmatic condition.

\* \* \* \* \*